United States Patent [19]

Robin et al.

[11] Patent Number: 4,710,505

[45] Date of Patent: Dec. 1, 1987

[54] ASYMMETRIC HETEROCYCLIC ESTER DERIVATIVES OF 1,4-DIHYDROPYRIDINE-3,5-DICARBOXYLIC ACIDS

[75] Inventors: Jacques Robin; Didier Pruneau, both of Dijon, France; Alain Bonenfant, Genève, Switzerland

[73] Assignee: Societe De Recherches Industrielles (S.O.R.I.), Paris, France

[21] Appl. No.: 830,927

[22] Filed: Feb. 19, 1986

[30] Foreign Application Priority Data

Feb. 20, 1985 [FR] France .................. 85 02412

[51] Int. Cl.[4] .............. A61K 31/44; C07D 405/12
[52] U.S. Cl. .................... 514/278; 514/336; 546/15; 546/283; 546/284; 549/30; 549/333; 549/454
[58] Field of Search .............. 546/15, 283, 284; 514/336, 278

[56] References Cited

U.S. PATENT DOCUMENTS 4,545,996 10/1985 Lafon .................. 514/629

FOREIGN PATENT DOCUMENTS 2364927 4/1978 France .
2514761 4/1983 France .

OTHER PUBLICATIONS

Schramm et al. Nature vol. 303, Jun. 1983 pp. 535–537.
Nishihata, et al., "Adjuvent Effects of Glyceryl Esters of Acetoacetic Acid on Rectal Absorption of Insulin and Inulin in Rabbits" J. of Pharmacuetical Sciences, vol. 72, No. 3, 1983, pp. 290–285.
French Patent Office Report on Corresponding French Application 8502412.

*Primary Examiner*—Jane T. Fan
*Attorney, Agent, or Firm*—Holman & Stern

[57] ABSTRACT

The present invention relates to new asymmetric heterocyclic ester derivatives of 1,4-dihydropyridine-3,5-dicarboxylic acids of the formula:

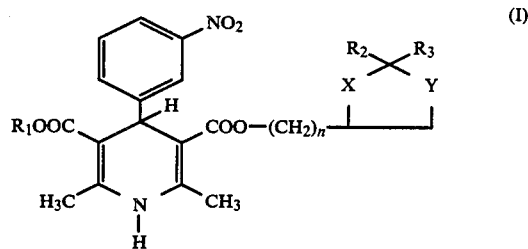

wherein $R_1$ is a $C_1$–$C_4$-alkyl group; X and Y, which are identical or different, each represent O or S, at least one of the symbols X and Y being different from S; n is an integer equal to 1 or 2; and $R_2$ and $R_3$, which are identical or different, each represent H, $CH_3$, $CF_3$, $C_6H_5$ or halogenophenyl, it being possible for $R_2$ and $R_3$, taken together, to form a 5-membered to 7-membered spirocycloaliphatic group with the C atom of the heterocyclic group to which they are bonded; and their optical iomers and diastereoisomers.

These new derivatives are useful as pharmaceuticals, in particular as vasodilators.

8 Claims, 12 Drawing Figures

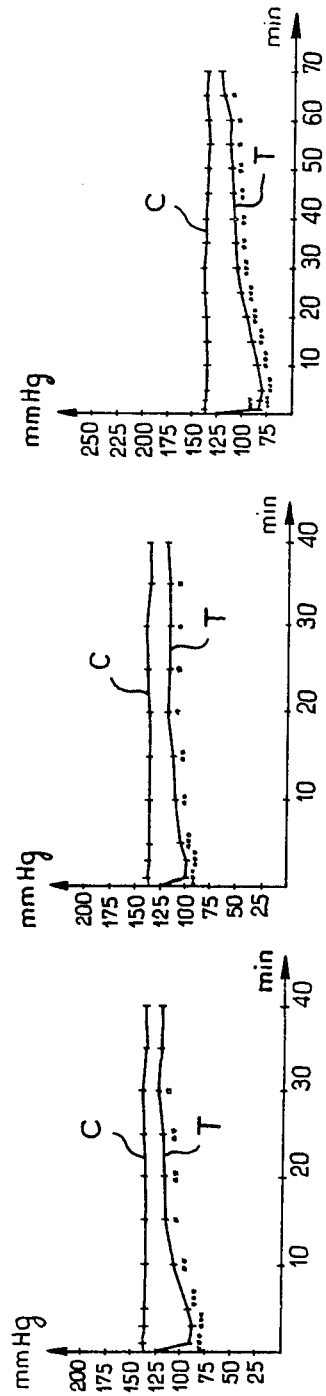

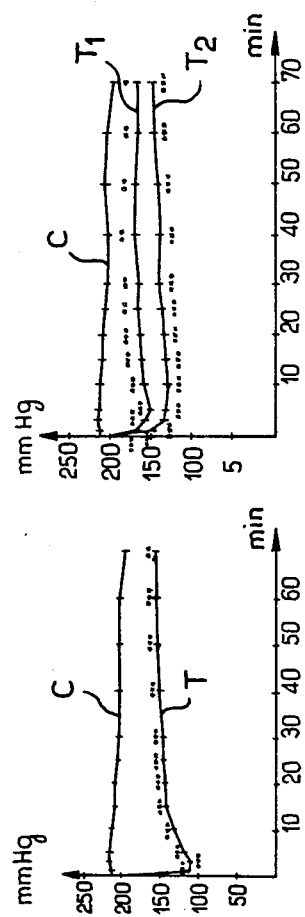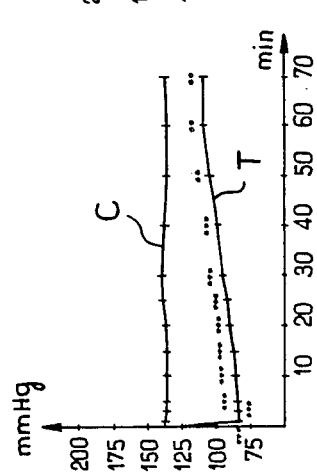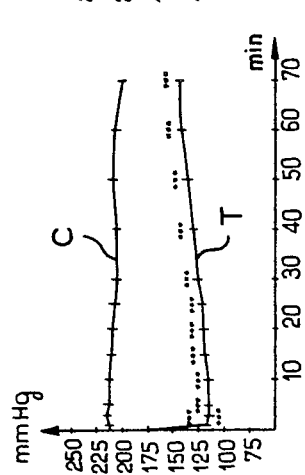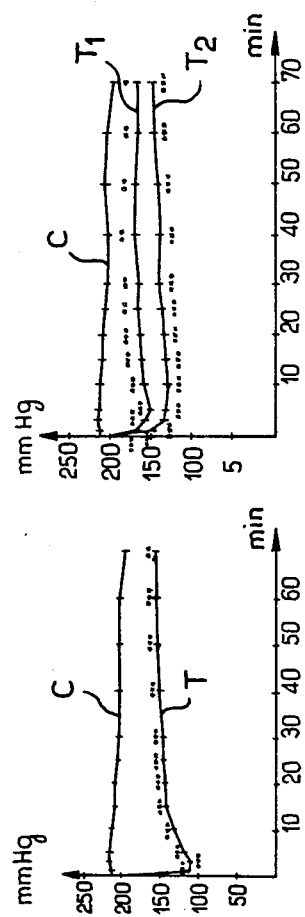
FIG. 4  FIG. 5  FIG. 6
FIG. 4a  FIG. 5a  FIG. 6a

ASYMMETRIC HETEROCYCLIC ESTER DERIVATIVES OF 1,4-DIHYDROPYRIDINE-3,5-DICARBOXYLIC ACIDS

The present invention relates to new derivatives belonging to the family of the asymmetric heterocyclic esters of 1,4-dihydropyridine-3,5-dicarboxylic acids. It also relates to the use of these new derivatives in therapy and the method for their preparation.

It is known that nifedipine, which corresponds to the systematic nomenclature dimethyl 1,4-dihydro-2,6-dimethyl-4-(2-nitrophenyl)pyridine-3,5-dicarboxylate and is described in Patent document U.S. Pat. No. 3,485,847, is a reference coronary vasodilator. It is also known that nicardipine, which corresponds to the systematic nomenclature methyl 2-(N-methyl-N-benzylamino)ethyl 1,4-dihydro-2,6-dimethyl-4-(3-nitrophenyl)pyridine-3,5-dicarboxylate and is described in Patent document U.S. Pat. No. 3,985,758, is a reference cerebral vasodilator. Finally, it is known that Patent document FR-A No. 2 514 761 has recommended asymmetric esters of 1,4-dihydro-2,6-dimethylpyridine-3,5-dicarboxylic acids of the formula:

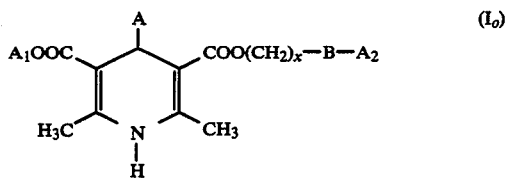

wherein, in particular, A is 2-nitrophenyl or 3-nitrophenyl; $A_1$ is $C_1-C_4$-alkyl; $A_2$ is H or $CH_3$; B is CO or a cyclic acetal or thioacetal group, such as ethylenedioxy, propylenedioxy, ethylenedithio or propylenedithio; and x is 1 or 2, as coronary and cerebral vasodilators.

It has now been found that the asymmetric ester derivatives according to the invention are vasodilators which differ from the symmetric derivative known in the prior art, namely nifedipine, and from the asymmetric derivatives mentioned above, namely nicardipine and the cyclic acetals and thioacetals of the formula $I_o$, in respect of (i) their structure, and (ii) their beneficial therapeutic properties, especially as regards their antihypertensive effects and their effects on the cardiac, femoral and coronary outputs.

The new derivatives according to the invention are selected from the group comprising:

(ii) the asymmetric heterocyclic ester derivatives of 1,4-dihydro-2,6-dimethylpyridine-3,5-dicarboxylic acid of the general formula:

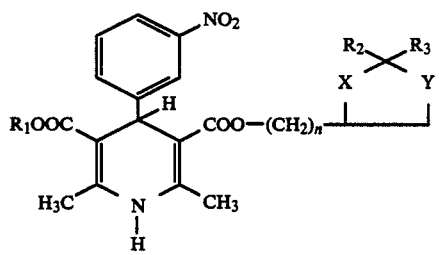

wherein $R_1$ is a $C_1-C_4$-alkyl group;

X and Y, which are identical or different, each represent O or S, at least one of the symbols X and Y being different from S;

n is an integer equal to 1 or 2; and $R_2$ and $R_3$, which are identical or different, each represent the hydrogen atom, the methyl group, the trifluoromethyl group, the phenyl group or a halogenophenyl group, it being possible for $R_2$ and $R_3$, taken together, to form a 5-membered to 7-membered spirocycloaliphatic group with the carbon atom of the heterocycle to which they are bonded; and (ii) their optical isomers and diastereoisomers.

The cyclopentyl, cyclohexyl and cycloheptyl groups may be mentioned in particular among the cycloaliphatic groups included in the definition of the groups $R_2$ and $R_3$ taken together.

The fluorine, chlorine and bromine atoms may be mentioned among the halogen atoms of the halogenophenyl group included in the definition of the groups $R_2$ and $R_3$. The 4-chlorophenyl, 3-fluorophenyl, 2,4-dichlorophenyl and 2,4-bibromophenyl groups may be mentioned in particular among the suitable halogenophenyl groups.

The compounds of the formula I above can be prepared according to a method known per se by the application of classical reaction mechanisms. The method recommended according to the invention consists in reacting a nitrobenzylideneacetoacetate of the formula:

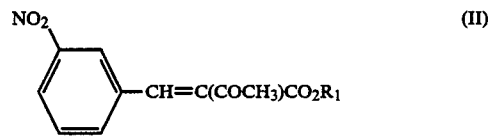

wherein $R_1$ is defined as above, with an aminocrotonate of the formula:

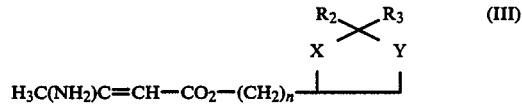

wherein n, X, Y, $R_2$ and $R_3$ are defined as indicated above, according to the so-called HANTZSCH reaction.

Advantageously, about 1 mol of II is reacted with about 1 mol of III in a polar organic solvent (especially a $C_1-C_4$-alkanol such as methanol, ethanol, isopropanol, n-butanol or t-butanol), for 1 to 24 hours, at a temperature between room temperature (15°-20° C.) and the reflux temperature of the reaction medium.

The compounds of the formula II are known substances which can be prepared according to the so-called KNOEVENAGEL reaction, cf. the review article by G. JONES, Organic Reactions 15, 204 (1975).

The compounds of the formula III are new products, the recommended preparation of which is as follows:

(1°) reaction of an alcohol of the formula:

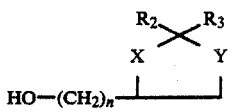 (IV)

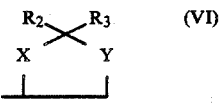 (VI)

wherein n, X, Y, R₂ and R₃ are defined as indicated above, with 5-acetal-2,2-dimethyl-4,6-dioxo-1,3-dioxane of the formula:

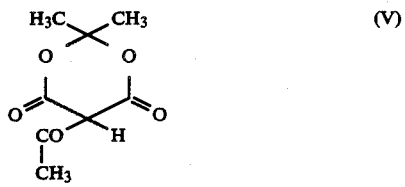 (V)

in an aromatic solvent (especially benzene, toluene or xylenes), at a temperature between room temperature (15°–20° C.) and the reflux temperature of the reaction medium, for 1 to 24 hours, to give a keto-ester of the formula:

and (2°) treatment of the resulting derivative of the formula VI with $NH_3$ in a chlorinated solvent (especially $CH_2Cl_2$ or $CHCl_3$) for 1 to 20 hours.

The compounds of the formulae III and IV can be used without prior purification. Advantageously, they are used after purification either by distillation (or recrystallization) or by flash chromatography (column chromatography under pressure) according to the technique described by W. C. STILL et al., J. Org. Chem. 43 (No. 14), 2923 (1978).

The keto-esters of the formula VI and the aminocrotonates of the formula III, which were prepared as indicated above and are involved in the synthesis of the compounds according to the invention, have been collated below, without implying a limitation, in Tables I and II respectively.

A number of compounds of the formula I according to the invention have been collated in Table III, also without implying a limitation.

TABLE I $$H_3C-\overset{O}{\underset{\|}{C}}-CH_2-\overset{O}{\underset{\|}{C}}-OR$$

| R | Reaction time (hours) | Yield % | Method of purification | Boiling point (°C.) | NMR |
|---|---|---|---|---|---|
| -CH₂- (1,3-dioxolane) | 2 | 77 | distillation | 100–110[b] | — |
| -CH₂- (2,2-dimethyl-1,3-oxathiolane) | 2 | 60 | flash chromatography [hexane/acetone (75:5) v/v] | — | 1.6–1.66 (6H, 2 singlets); 2.28 (3H, s); 3.1 (2H, m); 3.5 (2H, s); 4.4 (3H, m) |
| CH₂- (spiro cyclopentane dioxolane) | 9 | 80 | (a) | — | 1.69 (8H, m); 2.27 (3H, s); 3.5 (2H, s); 3.6–4.3 (5H, m) |
| CH₂- (spiro cyclohexane dioxolane) | 6 | 70 | flash chromatography [hexane/acetone (95:5) v/v] | — | 1.48 (10H, m); 2.25 (3H, s); 3.42 (2H, s); 3.6–4.3 (5H, m) |
| -CH₂-CH₂- (2,2-dimethyl-1,3-dioxolane) | 2 | 90 | (a) | — | 1.37 (6H, 2 singlets); 1.96 (2H, s); 2.26 (3H, s); 3.45 (2H, s); 3.5–4.3 (5H, m) |
| -CH₂- (2,2-dimethyl-1,3-dioxolane) | 15 | 85 | distillation | 95[c] | — |

TABLE I-continued
$$H_3C-\overset{O}{\overset{\|}{C}}-CH_2-\overset{O}{\overset{\|}{C}}-OR$$
| R | Reaction time (hours) | Yield % | Method of purification | Boiling point (°C.) | NMR |
|---|---|---|---|---|---|
| 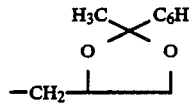 | 2 | 90 | (a) | — | — |
| 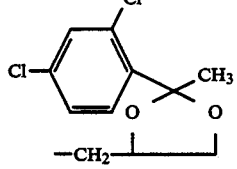 | 6 | 90 | (a) | — | — |
| 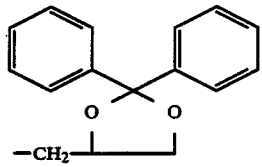 | 2 | 90 | (a) | — | — |
| 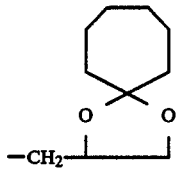 | 3 | 95 | (a) | — | — |
| 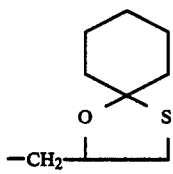 | 2 | 95 | (a) | — | — |
| 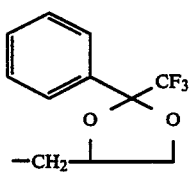 | 2 | 100 (crude) | (a) | — | 2.14–2.28 (3H, 2 singlets); 3.24–3.5 (2H, 2 singlets); 3.8–4.8 (5H, m) |
| 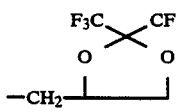 | 2 | 92 (crude) | (a) | — | 2.26 (3H, s); 3.5 (2H, s); 3.9–4.6 (5H, m) |
| 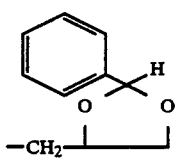 | 1 hour 30 minutes | 86 (crude) | (a) | — | 2.20–2.25 (3H, d); 3.45–3.5 (d) - 3.6 (s) 2H; 3.6–4.5 (5H, m); 5.55–5.8–5.94 (1H, 3 singlets); 7.2–7.6 (5H, m) |
Notes:
(a) without prior purification
(b) under 2 mm Hg (i.e. about 26.6 Pa)
(c) under 0.2 mm Hg (i.e. about 2.66 Pa)

TABLE II
$H_3C(NH_2)C=CH-CO_2R$
| R | Reaction time (hours) | Yield % | Method of purification | NMR |
|---|---|---|---|---|
| 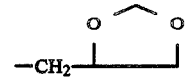 | 3 | 70 | (a) | 1.95 (3H, s); 3.7–4.3 (5H, m); 4.55 (1H, s); 5 (2H, 2 singlets) |
| 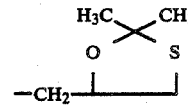 | 3 | 90 | (a) | 1.65 (6H, s); 1.9 (3H, s); 2.9–3.15 (2H, m); 4.2–4.3 (3H, m); 4.55 (1H, s) |
| 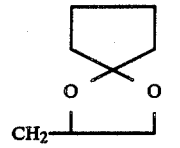 | 3 | 95 | (a) | 1.7 (8H, m); 1.9 (3H, s); 3.5–4.2 (5H, m); 4.55 (1H, s) |
| 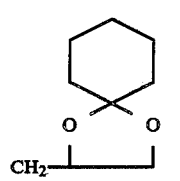 | 3 | 95 | (a) | 1.58 (10H, m); 1.9 (3H, s); 3.7–4.2 (5H, m); 4.55 (1H, s) |
| 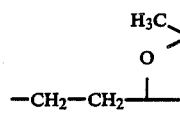 | 3 | 90 | flash chromatography [hexane/isopropanol (50:1) v/v] | 1.37 (6H, 2 singlets); 1.9 (3H, s); 1.95 (2H, m); 3.56–4.3 (5H, m); 4.5 (1H, s) |
| 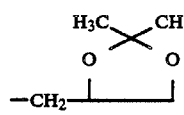 | 2 | 60 | recrystallization[b] | 1.37 (6H, 2 singlets); 1.9 (3H, s); 3.7–4.2 (5H, m); 4.56 (1H, s) |
| 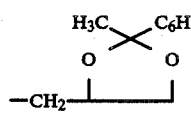 | 2 | 90 | (a) | — |
| 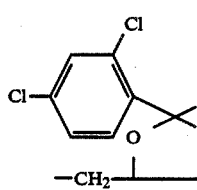 | 3 | 95 | (a) | — |
| 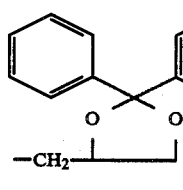 | 3 | 90 | (a) | — |
| 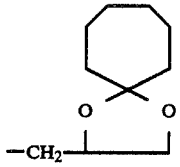 | 3 | 90 | (a) | — |

TABLE II-continued $H_3C(NH_2)C=CH-CO_2R$

| R | Reaction time (hours) | Yield % | Method of purification | NMR |
|---|---|---|---|---|
| -CH₂-(cyclohexane with O, S) | 4 | 90 | (a) | — |
| -CH₂-(C(Ph)(CF₃) with O, O) | 3 | 100 (crude) | (a) | 1.87–1.9 (3H, 2 singlets); 3.85–4.8 (6H, m) |
| -CH₂-(C(CF₃)₂ with O, O) | 2 | 100 (crude) | (a) | 1.9 (3H, s); 3.9–4.7 (unresolved signals including 1 singlet at 4.5) |
| -CH₂-(CH(Ph) with O, O) | 3 | 100 (crude) | (a) | 2.23–2.26 (3H, d); 3.4–3.6 (2H, m); 3.6–4.6 (1H, m); 5.55–5.8–5.96 (1H, 3 singlets); 7.2–7.6 (5H, m) |

Notes:
(a) without purification
(b) melting point: 87° C.

TABLE III

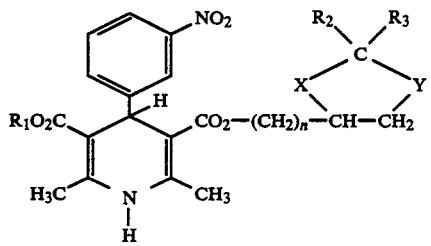

| Product | Code number | R₁ | R₂ | R₃ | n | X | Y | Melting point (°C.) |
|---|---|---|---|---|---|---|---|---|
| Ex. 1 | SR 1154 | CH₃ | CH₃ | CH₃ | 1 | O | O | 55 |
| Ex. 2 | SR 1308 | CH₃ | —(CH₂)₅— | | 1 | O | O | 62 |
| Ex. 3 | SR 1344 | CH₃ | H | H | 1 | O | O | 119 |
| Ex. 4 | SR 1377 | CH₃ | CH₃ | CH₃ | 2 | O | O | (a) |
| Ex. 5 | SR 1399 | CH₃ | —(CH₂)₄— | | 1 | O | O | (b) |
| Ex. 6 | SR 1411 | CH₃ | CH₃ | CH₃ | 1 | O | O | 82 |
| Ex. 7 | SR 1433 | CH₃ | CH₃ | phenyl | 1 | O | O | 50 |
| Ex. 8 | SR 1457 | CH₃ | phenyl | phenyl | 1 | O | O | 75 |
| Ex. 9 | 2.0050 | CH₃ | —(CH₂)₅— | | 1 | O | S | 50 |
| Ex. 10 | 2.0054 | CH₃ | —(CH₂)₆— | | 1 | O | O | 50 |

TABLE III-continued

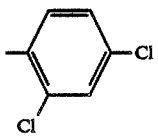

| Product | Code number | R₁ | R₂ | R₃ | n | X | Y | Melting point (°C.) |
|---|---|---|---|---|---|---|---|---|
| Ex. 11. | SR 1458 | CH₃ | CH₃ | 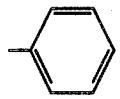 | 1 | O | O | 50 |
| Ex. 12 | 2.0095 | CH₃ | CF₃ | 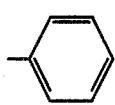 | 1 | O | O | (c) |
| Ex. 13 | 2.0128 | CH₃ | CF₃ | CF₃ | 1 | O | O | 113 |
| Ex. 14 | 2.0182 | CH₃ | H | 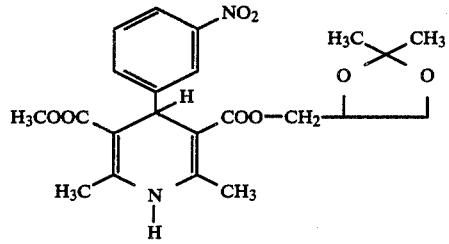 | 1 | O | O | (d) |

Notes:
(a) viscous product
(b) yellow foam
(c) foam melting over the range from 65° to 80° C.
(d) foam melting over the range from 55° to 80° C.

The enantiomeric isomers and diastereoisomers are separated from the corresponding racemates according to a method known per se, especially by fractional crystallization, resolution or another method.

A therapeutic composition recommended according to the invention contains, in association with a physiologically acceptable excipient, at least one compound selected from the group comprising the derivatives of the formula I above, the enantiomeric isomers and the diastereoisomers.

Of course, in a composition of this type, the active principle is used in a pharmaceutically effective quantity.

Further advantages and characteristics of the invention will be understood more clearly from the following description of preparative examples and results of pharmacological experiments. All this information is given by way of illustration and does not imply a limitation.

PREPARATION I

Preparation of methyl (2,2-dimethyl-1,3-dioxolan-4-yl)methyl 1,4-dihydro-2,6-dimethyl-4-(3-nitrophenyl)pyridine-3,5-dicarboxylate

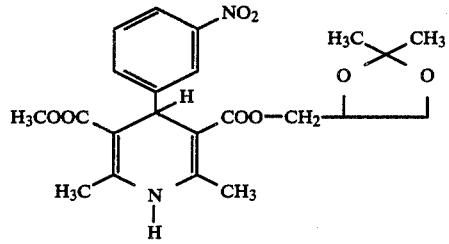

EXAMPLE 1

Code No.: SR 1154

A mixture of 2.5 g (0.01 mole) of methyl 3-nitrobenzylideneacetylacetate, 2.2 g (0.01 mole) of (2,2-dimethyl-1,3-dioxolan-4-yl)methyl 3-aminocrotonate and 20 ml of tert.-butanol is heated at 95°-100° C. for 13 hours. The solvent is evaporated off and the crude foam obtained (3.4 g) is dissolved in 5 ml of acetone and then purified by chromatography on a column of silica gel according to the flash chromatography technique referred to above, elution being carried out with an acetone/hexane mixture (1:5) v/v. This gives 3.10 g (yield: 69.5%) of SR 1154. Melting point=55° C.

NMR spectrum (CDCl₃) δ (intensity, multiplicity): 1.34 (3H, s); 1.39 (3H, s); 2.36 (6H, s); 3.6–4.2 (5H, m); 3.6 (3H, s); 5.12 (1H, s); 5.89 (1H, s); 7.4–8.09 (4H, m).

PREPARATION II

Preparation of methyl (1,4-dioxaspiro[4,5]decan-2-yl)methyl 1,4-dihydro-2,6-dimethyl-4-(3-nitrophenyl)-pyridine-3,5-dicarboxylate

EXAMPLE 2

Code No.: SR 1308

A mixture of 4.8 g ($1.88 \times 10^{-2}$ mole) of methyl 3-nitrobenzylideneacetylacetate, 4.68 g ($1.88 \times 10^{-2}$ mole) of (1,4-dioxaspiro[4,5]decan-2-yl)methyl 3-aminocrotonate and 40 ml of tert.-butanol is heated at 90°–95° C. for 12 hours. The solvent is evaporated off and the product obtained is purified by flash chromatography, elution being carried out with an acetone/hexane mixture (1:5) v/v. This gives 4.2 g (yield: 46%) of SR 1308. Melting point = 62° C.

NMR spectrum (CDCl$_3$) δ (intensity, multiplicity): 1.58 (10H, s); 2.37 (6H, s); 3.65–4.12 (5H, m); 3.65 (3H, s); 5.12 (1H, s); 5.80 (1H, s); 7.4–8.08 (4H, m).

PREPARATION III

Preparation of methyl 2-[(2,2-dimethyl-1,3-dioxolan-4-yl)ethyl]1,4-dihydro-2,6-dimethyl-4-(3-nitrophenyl)-pyridine-3,5-dicarboxylate

EXAMPLE 4

Code No.: SR 1377

A mixture of 8 g ($3.2 \times 10^{-2}$ mole) of methyl 3-nitrobenzylideneacetylacetate, 9.6 g ($4.1 \times 10^{-2}$ mole) of 2-(2,2-dimethyl-1,3-dioxolan-4-yl)ethyl 3-aminocrotonate and 40 ml of tert.-butanol is heated under reflux for 5 hours. The solvent is evaporated off and the crude product obtained is purified by flash chromatography, elution being carried out firstly with a toluene/ethyl acetate/diisopropyl ether mixture (90:2:2) v/v and secondly with a toluene/ethyl acetate/diisopropyl ether mixture (90:1:1) v/v. This gives 3.2 g (yield: 22%) of SR 1377 in the form of an oil.

NMR spectrum (CDCl$_3$) δ (intensity, multiplicity): 1.3 (3H, s); 1.38 (3H, s); 1.84 (2H, m); 2.37 (6H, s); 3.65 (3H, s); 3.5–4.27 (5H, m); 5.11 (1H, s); 5.98 (1H, s); 7.4–8.1 (4H, m).

PREPARATION IV

Preparation of methyl (1,4-dioxaspiro[4,4]nonan-2-yl)methyl 1,4-dihydro-2,6-dimethyl-4-(3-nitrophenyl)pyridine-3,5-dicarboxylate

EXAMPLE 5

Code No.: SR 1399

A mixture of 4.6 g ($1.79 \times 10^{-2}$ mole) of methyl 3-nitrobenzylideneacetylacetate, 4.3 g ($1.78 \times 10^{-2}$ mole) of (1,4-dioxaspiro[4,4]nonan-2-yl)methyl 3-aminocrotonate and 45 ml of tert.-butanol is heated under reflux for 12 hours. The solvent is evaporated off and the crude product obtained is purified by flash chromatography, elution being carried out with a hexane/acetone mixture (9:1) v/v. This gives 2.2 g (yield: 26%) of SR 1399 in the form of a yellow foam.

NMR spectrum (CDCl$_3$) δ (intensity, multiplicity): 1.7 (8H, s); 2.37 (6H, s); 3.65 (3H, s); 3.65–5.12 (5H, m); 5.12 (1H, s); 5.87 (1H, s); 7.27–8.09 (4H, m).

The compounds below are obtained by following the procedure given above:

EXAMPLE 3

(SR 1344), melting point = 119° C.

NMR spectrum (CDCl$_3$) δ (intensity, multiplicity): 2.37 (6H, s); 3.6 (3H, s); 3.6–4.24 (5H, m); 4.87 (1H, s); 4.99 (1H, s); 5.11 (1H, s); 6.15 (1H, s); 7.4–8.1 (4H, m).

EXAMPLE 6

(SR 1411), melting point = 82° C.

NMR spectrum (CDCl$_3$) δ (intensity, multiplicity): 1,6 (3H, s); 1.65 (3H, s); 2.36–2.38 (6H, 2 singlets); 2.95 (2H, m); 3.66 (3H, s); 4.2–4.37 (3H, m); 5.84 (1H, s); 6.44 (1H, s); 7.38–8.11 (4H, m).

EXAMPLE 7

(SR 1433), melting point = 50° C.

NMR spectrum (CDCl$_3$) δ (intensity, multiplicity): 1.6 (3H, 2 singlets); 2.37 (6H, 2 singlets); 3.6 (3H, s); 3.5–4.2 (5H, m); 5.05 (1H, m); 6.04 (1H, m); 7.2–7.7 (7H, m); 7.9–8.1 (2H, m).

EXAMPLE 8

(SR 1457), melting point = 75° C.

NMR spectrum (CDCl$_3$) δ (intensity, multiplicity): 2.33 (6H, 2 singlets); 3.64 (3H, s); 3.5–4.2 (5H, m); 5.1 (1H, s); 5.9 (1H, s); 7.2–7.7 (12H, m); 7.8–8.1 (2H, m).

EXAMPLE 9 melting point = 50° C.

NMR spectrum (CDCl$_3$) δ (intensity, multiplicity): 1.4–1.85 (10H, m); 2.38 (6H, s); 2.84 (2H, m); 3.65 (3H, s); 4.2 (3H, m); 5.13 (1H, s); 5.80 (1H, s); 7.2–7.7 (2H, m); 8.0–8.1 (2H, m).

EXAMPLE 10 melting point = 50° C.

NMR spectrum (CDCl$_3$) δ (intensity, multiplicity): 1.5–1.8 (12H, m); 2.36 (6H, s); 3.65 (3H, s); 3.5–4.2 (5H, m); 5.12 (1H, s); 5.96 (1H, s); 7.2–7.7 (2H, m); 8.0–8.1 (2H, m).

EXAMPLE 11 melting point = 50° C.

NMR spectrum (CDCl$_3$) δ (intensity, multiplicity): 1.74 (3H, m); 2.35 (6H, m); 3.66 (3H, s); 3.5–4.2 (5H, m); 5.1 (1H, m); 5.88 (1H, m); 7.2–7.7 (7H, m); 7.9–8.1 (2H, m).

EXAMPLE 12

NMR spectrum (CDCl$_3$) δ (intensity, multiplicity): 2.22–2.34–2.37–2.39 (6H, 4 singlets); 3.5–4.6 (8H, m including 1 singlet at 3.66); 4.96–5.04–5.14 (1H, 3 singlets); 6.0 (1H, s); 7.1–8.06 (9H, m).

EXAMPLE 13 melting point = 113° C.

NMR spectrum (CDCl$_3$) δ (intensity, multiplicity): 2.37 (6H, s); 3.4–4.44 (8H, m); 5.1 (1H, s); 5.9 (1H, s); 7.3–8.07 (4H, m).

EXAMPLE 14

NMR spectrum (CDCl$_3$) δ (intensity, multiplicity): 2.34–2.38 (6H, 2 singlets); 3.64–3.6 (3H, 2 singlets); 3.5–4.4 (5H, m); 5.11–5.14 (1H, 2 singlets); 5.8–5.88–5.9 (1H, 3 singlets); 6.1 (1H, s); 7.2–8.1 (9H, m).

There follows a summary of the results of the pharmacological experiments which were undertaken on the one hand with the compounds according to the invention and on the other hand, for comparison, with products known in the prior art.

I. RELAXING EFFECT ON ISOLATED RABBIT AORTA CONTRACTED BY KCl

The thoracic aortae of male rabbits are removed, cut into narrow strips and placed under tension in an oxygenated survival medium. The contractions of these arteries, the amplitude of which is measured using a myograph, are induced by a 127 mM solution of KCl [R. Towart et al., Arzneim.-Forsch./Drug Res. 32, 338–346 (1982)]. The compounds studied are dissolved in a mixture of anhydrous ethanol and double distilled water (1:1) v/v, the percentage of ethanol in the baths being less than or equal to 0.3% at the end of the experiment. When the contraction plateau is reached, the compound is added to the medium in increasing doses every 15 minutes. As examples, the doses causing a 50% relaxation of the precontracted arteries ($ED_{50}$) are given in Table IV and compared with nicardipine and nifedipine.

In this experiment demonstrating products which block the entry of calcium into the arterial smooth muscle, the compounds of the invention are active since their $ED_{50}$ is of the same order of magnitude as that of nicardipine and nifedipine.

II. ANTIHYPERTENSIVE ACTIVITY

1. Oral administration

Spontaneously hypertensive rats aged between 16 and 20 weeks are used. The systolic pressure is measured by plethysmography and the heart rate is obtained from the pressure graph. The compounds studied are administered orally. The results obtained are collated in Table V below.

2. Intravenous administration

Spontaneously hypertensive rats aged between 16 and 20 weeks are used. They are anesthetized with diethyl ether, a cannula is inserted into the caudal artery to measure the arterial pressure and a catheter is inserted into the right jugular vein to administer the compounds as described previously (L. S. Watson and L. T. Ludden, New Antihypertensive Drugs, pages 87–96, Spectrum Publication, Inc., 1976).

By way of example, the attached figures show the variation in the arterial pressure of conscious, spontaneously hypertensive rats after intravenous administration of a single dose of the compounds of Examples 2, 7, 8 and 11, nicardipine and nifedipine. Each curve C relates to the control group receiving only the vehicle and each curve T relates to the treated group [n (number of animals per group)=4–7]. The said groups are compared either by analysis of variance, if the variances are homogenous (Bartlett's homocedasticity test), or by Kruskall-Wallis's non-parametric test (the statistically significant results being represented as follows:

\* for $p<0.05$;
\*\* for $p<0.01$; and
\*\*\* for $p<0.001$).

FIGS. 1–6 relate to the variation in systolic pressure, expressed in mm Hg (1 mm Hg corresponds approximately to $1.333 \times 10^2$ Pa), as a function of time, expressed in minutes, and FIGS. 1a–6a relate to the variation in diastolic pressure, also expressed in mm Hg, as a function of time, expressed in minutes, for the treated groups (curves T) compared with the corresponding control groups (curves C), the doses of products administered being as follows:

FIGS. 1 and 1a: nifedipine at 300 μg/kg i.v.,
FIGS. 2 and 2a: nicardipine at 30 μg/kg i.v.,
FIGS. 3 and 3a: Example 2 at 30 μg/kg i.v.,
FIGS. 4 and 4a: Example 7 at 100 μg/kg i.v.,
FIGS. 5 and 5a: Example 8 at 300 μg/kg i.v., and
FIGS. 6 and 6a: Example 11 at 30 and 100 μg/kg i.v. (curves $T_1$ and $T_2$).

The compound of Example 2 causes a greater drop in systolic and diastolic pressures than nicardipine at the same dose and nifedipine at 10 times the dose. The duration of the antihypertensive effect of the compounds of Examples 2, 7, 8 and 11 is notably longer than that of nicardipine and nifedipine.

III. HEMODYNAMIC EFFECTS ON ANESTHETIZED DOGS

Mongrel dogs are anesthetized with pentobarbital sodium (25 mg/kg i.v.). Each animal is placed under artificial respiration and a catheter is introduced into the aorta to measure the arterial pressure. The outputs of the aorta (O. Aor.), right femoral artery (O. Fem.) and left coronary artery (descending part) (O. Cor.) are measured continuously by means of electromagnetic rings. The total peripheral resistances (T.P.R.) are also calculated.

The compounds are administered intraduodenally (i.d.) at doses chosen so as to cause a drop in diastolic pressure (D.P.) of about 40% (from 34.5 to 44.2%). The results obtained are collated in Table VI.

It is found that the compounds of Examples 1 and 2 cause a greater drop in total peripheral resistances than nicardipine and nifedipine, the duration of this effect being considerably longer. The cardiac, femoral and coronary outputs are increased for a longer time and to a greater extent with the compounds of Examples 1 and 2 than with nicardipine and nifedipine.

IV. ACUTE TOXICITY

The $LD_{50}$ was determined by intravenous administration to male Wistar rats weighing 300 g.

The $LD_{50}$ values are respectively 11.8 mg/kg for nicardipine, 13.2 mg/kg for nifedipine, 22.5 mg/kg for the compound of Example 1, 27.9 mg/kg for the compound of Example 2, 34.2 mg/kg for the compound of Example 6, 17.8 mg/kg for the compound of Example 7, 44.4 mg/kg for the compound of Example 8 and 38.9 mg/kg for the compound of Example 11.

V. CONCLUSIONS

The results of the abovementioned experiments demonstrate that the compounds according to the invention, and in particular those of Examples 1, 2, 7, 8 and 11, are distinguished from the products known in the prior art
- by a longer-lasting antihypertensive effect,
- by an increase in the volume and duration of the cardiac, femoral and coronary outputs,
- by a substantial reduction in the diastolic pressure having regard to the lowering of the total peripheral resistances, and
- by a lower acute toxicity.

The compounds according to the invention, which are noteworthy vasodilators, are particularly useful on the one hand in the treatment of hypertension and on the other hand in the prevention and treatment of peripheral, cerebral and coronary circulatory disorders. In clinical trials, it was found that the characteristic of increasing the cardiac output and greatly lowering the peripheral resistances makes the products according to the invention very valuable, especially in the treatment of cardiac insufficiency or hypertension, more particularly in the elderly.

Possible methods of administration of the products according to the invention to man are, in particular, oral at a dose of 0.005 to 10 mg/kg or intravenous at a dose of 1 to 300 μg/kg.

Also recommended according to the invention is the use of a substance selected from the group comprising the derivatives of the formula I, their optical isomers and their diastereoisomers, for the preparation of a vasodilating drug intended for use in human therapy for counteracting hypertension and cardiac insufficiency.

TABLE IV

RELAXING EFFECT ON RABBIT AORTA DEPOLARIZED BY KCl

| PRODUCT | $ED_{50}$ (M) |
| --- | --- |
| Ex. 1 | $3.1 \times 10^{-8}$ |
| Ex. 2 | $5.0 \times 10^{-8}$ |
| Ex. 3 | $4.3 \times 10^{-8}$ |
| Ex. 4 | $3.2 \times 10^{-8}$ |
| Ex. 6 | $3.5 \times 10^{-8}$ |
| Ex. 8 | $>5 \times 10^{-6}$ |
| Ex. 11 | $>5 \times 10^{-6}$ |
| Ex. 12 | $5 \times 10^{-6}$ |
| Ex. 13 | $>5 \times 10^{-6}$ |
| Ex. 14 | $>5 \times 10^{-6}$ |
| CP 1 (a) | $2.5 \times 10^{-7}$ |
| nicardipine | $2.6 \times 10^{-8}$ |
| nifedipine | $2.2 \times 10^{-8}$ |

Note
(a) Comparison product (described in Example 1 of Patent document FR-A-2 514 761), namely methyl 2,2-ethylenedioxypropyl 2,6-dimethyl-4-(3-nitrophenyl)-1,4-dihydropyridine-3,5-dicarboxylate.

TABLE V

ANTIHYPERTENSIVE ACTIVITY IN SPONTANEOUSLY HYPERTENSIVE RATS
oral administration

| PRODUCT | DOSE (mg/kg) | % variation Systolic pressure* | Heart rate* |
| --- | --- | --- | --- |
| Ex. 1 | 30 | −28.4 ± 7.3 (8 to 16) | +16.4 ± 9.6 (2 to 4) |
| Ex. 2 | 30 | −45.4 ± 6.3 (>24) | +24.5 ± 9.7 (8 to 16) |
| Ex. 5 | 30 | −40.4 ± 9.4 (4 to 6) | +19.3 ± 9.1 (4) |
| Ex. 6 | 30 | −35.1 ± 9.2 (4 to 6) | +21.4 ± 12.8 (1 to 2) |
| Ex. 7 | 30 | −40.5 ± 5.1 (>24) | +36.4 ± 12.5 (8 to 24) |
| Ex. 8 | 30 | −37.0 ± 9.0 (>24) | +12.4 ± 11.3 (2 to 4) |
| Ex. 11 | 30 | −54.0 ± 5.9 (>24) | +34.0 ± 17.0 (8 to 24) |
| Ex. 12 | 10 | −41.4 ± 10.0 (>24) | +31.2 ± 13.8 (8 to 24) |
| Ex. 13 | 30 | −31.6 ± 8.7 (>24) | +25.0 ± 11.2 (6 to 8) |
| Ex. 14 | 30 | −58.4 ± 32.9 (>24) | +19.9 ± 14.8 (>24) |
| CP 1 (a) | 30 | −11.6 ± 6.0 (0) | 0 |
| nicardipine | 30 | −46.2 ± 6.8 (8 to 24) | +21.3 ± 10.8 (8 to 24) |
| nifedipine | 30 | −35.2 ± 4.7 (8 to 24) | +35.4 ± 15 (4 to 6) |

Notes:
*the duration of the effect in hours has been indicated in brackets
(a) see note a in Table IV

TABLE VI

HEMODYNAMIC EFFECTS ON ANESTHETIZED DOGS
intraduodenal administration

| Product | Dose (mg/kg) | % variation (a) (b) D.P. | T.P.R. | O. Aor. | O. Fem. | O. Cor. |
| --- | --- | --- | --- | --- | --- | --- |
| Ex. 1 | 0.5 | −42.6 (120) | −65 (300) | +124 (120) | +114 (270) | +73.6 (NS) |
| Ex. 2 | 0.5 | −41.2 (240) | −53.4 (300) | +40.2 (300) | +180.5 (300) | +89.5 (300) |
| Nifedipine | 0.35 | −44.2 (240) | −48.6 (180) | +20.5 (NS) | +76.4 (10) | +66.4 (NS) |
| Nicardipine | 0.5 | −34.5 (150) | −40.5 (90) | +25 (NS) | +70.6 (NS) | +62.2 (NS) |

Notes:
(a): the duration of the effect, expressed in minutes, is given in brackets.
(b): the letters NS (not significant) indicate that the variation in the measured effect was not statistically different from that in a group of dogs receiving the vehicle. The groups were compared either by analysis of variance, if the variances were homogeneous (Bartlett's homocedasticity test), or by Kruskall-Wallis's non-parametric test.

What is claimed is:

1. An asymmetric heterocyclic ester compound of a 1,4-dihydropyridine-3,5-dicarboxylic acid, selected from the group consisting of:
   (i) 1,4-dihydro-2,6-dimethylpyridine-3,5-dicarboxylic acid esters of the formula:

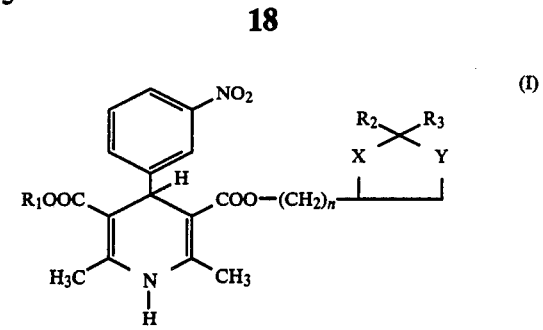

wherein $R_1$ is a $C_1$-$C_4$-alkyl group; X and Y, which are identical or different, each represent O or S, at least one of the symbols X and Y being different from S; n is an integer equal to 1 or 2; and $R_2$ and $R_3$, which are identical or different, each represent the hydrogen atom, the methyl group, the trifluoromethyl group, the phenyl group or a halogenophenyl group, wherein $R_2$ and $R_3$ taken together, can form a 5-membered to 7-membered spirocycloalkyl group with the carbon atom of the heterocycle to which they are bonded;
   (ii) optical isomers thereof; and
   (iii) diastereoisomers thereof.

2. A compound according to claim 1, wherein $R_2$ and $R_3$ form a cyclopentyl, cyclohexyl or cycloheptyl radical with the carbon atom of the heterocyclic group to which they are bonded.

3. A compound according to claim 1, wherein $R_2$ and $R_3$, which are identical or different, each represent H, $CH_3$, $CF_3$, $C_6H_5$ or 2,4-dichlorophenyl.

4. A compound according to claim 1, which is methyl (2,2-dimethyl-1,3-dioxolan-4-yl)methyl 1,4-dihydro-2,6-dimethyl-4-(3-nitrophenyl)pyridine-3,5-dicarboxylate.

5. A compound according to claim 1, which is methyl (1,4-dioxaspiro[4,5]decan-2-yl)methyl 1,4-dihydro-2,6-dimethyl-4-(3-nitrophenyl)pyridine-3,5-dicarboxylate.

6. A compound according to claim 1, which is methyl (2,2-diphenyl-1,3-dioxolan-4-yl)methyl 1,4-dihydro-2,6-dimethyl-4-(3-nitrophenyl)pyridine-3,5-dicarboxylate.

7. A pharmaceutical composition comprising, in association with physiologically acceptable excipient, an effective vasodilating amount of a compound selected from the group consisting of
   (1) 1,4-dihydro-2,6-dimethylphyidine-3,5-dicarboxylic acid esters of the formula I according to claim 1;
   (ii) optical isomers thereof; and
   (iii) diastereoisomers thereof.

8. A method of treatment of hypertension and cardiac insufficiency, which comprises administering to a human being an effective vasodilating amount of a compound selected form the group consisting of
   (i) 1,4-dihydro-2,6-dimethylpyridine-3,5-dicarboxylic acid esters of the formula of claim 1;
   (ii) optical isomers thereof; and
   (iii) diastereoisomers thereof.

* * * * *